United States Patent
Carling et al.

(10) Patent No.: US 6,608,062 B1
(45) Date of Patent: Aug. 19, 2003

(54) IMIDAZO-TRIAZINE DERIVATIVES AS LIGANDS FOR GABA RECEPTORS

(75) Inventors: William Robert Carling, Harlow (GB); Alexander Richard Guiblin, Harlow (GB); Kevin William Moore, Harlow (GB); Christopher Richard Moyes, Harlow (GB); Michael Rowley, Harlow (GB); Leslie Joseph Street, Harlow (GB)

(73) Assignee: Merck Sharp & Dohme Ltd., Hoddesdon ( * ) Notice: Subject to any disclaimer, the term of this patent is extended or adjusted under 35 U.S.C. 154(b) by 54 days.

(21) Appl. No.: 10/069,437

(22) PCT Filed: Aug. 17, 2000

(86) PCT No.: PCT/GB00/03199

§ 371 (c)(1),
(2), (4) Date: Feb. 19, 2002

(87) PCT Pub. No.: WO01/14377

PCT Pub. Date: Mar. 1, 2001

(30) Foreign Application Priority Data

Aug. 23, 1999 (GB) .............................................. 9919957

(51) Int. Cl.[7] ...................... C07D 487/04; A61K 31/53; A61P 25/22
(52) U.S. Cl. ....................................... 514/243; 544/184
(58) Field of Search ........................... 544/184; 514/243

(56) References Cited

U.S. PATENT DOCUMENTS 3,422,194 A    1/1969    Loev Bernard ............. 424/249

FOREIGN PATENT DOCUMENTS

| WO | WO 9804559 | 2/1998 |
| WO | WO 0023449 | 4/2000 |

OTHER PUBLICATIONS

Crestani et al. Curr. Opin. Pharmacol. 1(1):22–25, 2001.*

* cited by examiner

*Primary Examiner*—Venkataraman Balasubramanian
(74) *Attorney, Agent, or Firm*—J. Eric Thies; Melvin Winokur; Baerbel B. Brown

(57) ABSTRACT

A class of substituted 1,2,4-triazolo[4,3-]pyridazine derivatives, possessing an optionally substituted cycloalkyl, phenyl or heteroaryl substituent at the 3-position, a substituted alkoxy moiety at the 6-position, and an optionally substituted bicycloalkyl ring system at the 7-position, are selective ligands for $GABA_A$ receptors, in particular having high affinity for the $\alpha 2$ and/or $\alpha 3$ subunit thereof, and are accordingly of benefit in the treatment and/or prevention of disorders of the central nervous system, including anxiety and convulsions.

9 Claims, No Drawings

IMIDAZO-TRIAZINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB00/03199, filed Aug. 17, 2000, which claims priority under 35 U.S.C. §119 from GB Application No. 9919957.2, filed Aug. 23, 1999.

The present invention relates to a class of substituted imidazo-triazine derivatives and to their use in therapy. More particularly, this invention is concerned with substituted imidazo[1,2-d][1,2,4]triazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta2/3\gamma2$, $\alpha3\beta\gamma2/3$, $\alpha2\beta\gamma1$, $\alpha5\beta3\gamma2/3$, $\alpha6\beta\gamma2$, $\alpha6\beta\delta$ and $\alpha4\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

The present invention provides a class of imidazo-triazine derivatives which possess desirable binding properties at various $GABA_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

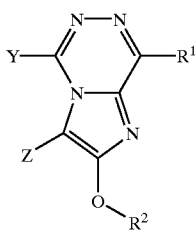

(I)

wherein

Y represents hydrogen, $C_{1-6}$ alkyl or $C_{3-7}$ cycloalkyl;

Z represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl or di($C_{1-6}$)alkylamino, any of which groups may be optionally substituted;

$R^1$ represents $C_{3-7}$ cycloalkyl, phenyl, furyl, thienyl or pyridinyl, any of which groups may be optionally substituted; and $R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

The present invention also provides a compound of formula I as depicted above, or a salt or prodrug thereof, wherein Y represents hydrogen or $C_{1-6}$ alkyl; and Z, $R^1$ and $R^2$ are as defined above.

The groups Z, $R^1$ and $R^2$ may be unsubstituted, or substituted by one or more, suitably by one or two, substituents. In general, the groups Z, $R^1$ and $R^2$ will be unsubstituted or monosubstituted. Examples of optional substituents on the groups Z, $R^1$ and $R^2$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$) alkoxy. Particular substituents include $C_{1-6}$ alkyl and halogen, specifically methyl, ethyl, fluoro or chloro, and especially methyl, fluoro or chloro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical $C_{6-8}$ bicycloalkyl groups include bicyclo[2.1.1] hexyl and bicyclo[2.2.1]heptyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Typical values for the substituent Y include hydrogen, methyl, ethyl and cyclopropyl, especially hydrogen or methyl. In one embodiment, Y represents hydrogen. In another embodiment, Y represents methyl. In a further embodiment, Y represents ethyl. In a still further embodiment, Y represents cyclopropyl.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, phenyl, fluorophenyl, chlorophenyl, pyrrolidinyl, methyl-pyrrolidinyl, piperidinyl, morpholinyl, thiomorpholinyl, pyridinyl, furyl, thienyl, chloro-thienyl and diethylamino.

Illustrative values of Z include cyclobutyl, cyclopentyl, cyclohexyl, phenyl, fluorophenyl, chlorophenyl and thienyl.

Representative values of Z include cyclobutyl, cyclopentyl, phenyl and chlorophenyl.

In a particular embodiment, the substituent Z represents $C_{3-7}$ cycloalkyl, either unsubstituted or substituted by $C_{1-6}$ alkyl, especially methyl. Favourably, Z represents cyclobutyl, cyclopentyl or cyclohexyl, specifically cyclobutyl or cyclopentyl, especially cyclobutyl.

In another embodiment, Z represents tert-butyl.

In a further embodiment, Z represents phenyl.

In a still further embodiment, Z represents fluorophenyl, especially 2-fluorophenyl.

In a yet further embodiment, Z represents chlorophenyl, especially 3-chlorophenyl.

In one more embodiment, Z represents thienyl, especially thien-2-yl.

Examples of typical optional substituents on the group $R^1$ include methyl, fluoro and methoxy, especially fluoro.

Representative values of $R^1$ include cyclopropyl, phenyl, methylphenyl, fluorophenyl, difluorophenyl, methoxyphenyl, furyl, thienyl, methyl-thienyl and pyridinyl. More particularly, $R^1$ may represent unsubstituted, monosubstituted or disubstituted phenyl. Most particularly, $R^1$ represents phenyl, fluorophenyl or difluorophenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^2$ represents an optionally substituted triazolylmethyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, particularly methyl or ethyl, especially methyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

A favoured value of $R^2$ is methyl-triazolylmethyl.

Another favoured value of $R^2$ is ethyl-triazolylmethyl.

A particular sub-class of compounds according to the invention is represented by the compounds of formula IIA, and salts and prodrugs thereof:

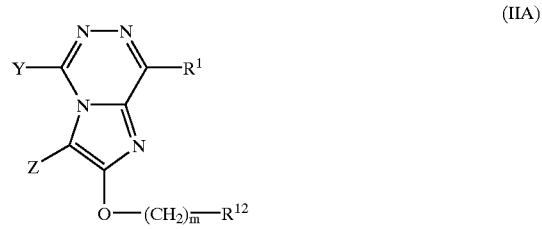

(IIA)

wherein

Y, Z and $R^1$ are as defined with reference to formula I above;

m is 1 or 2, preferably 1; and $R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted by one or more substituents.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, particularly methyl or ethyl, especially methyl.

Particular values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, ethyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{12}$ is methyl-triazolyl.

Another favoured value of $R^{12}$ is ethyl-triazolyl.

A particular subset of the compounds of formula IIA above is represented by the compounds of formula IIB, and pharmaceutically acceptable salts thereof:

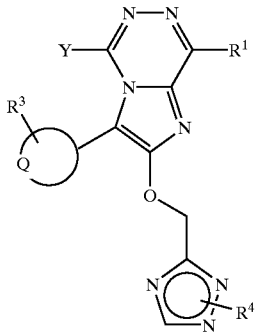

(IIB)

wherein
Y and $R^1$ are as defined with reference to formula I above;
Q represents the residue of a cyclopropyl, cyclobutyl, cyclopentyl, cyclohexyl, phenyl or thienyl ring;
$R^3$ represents hydrogen, methyl, fluoro or chloro; and
$R^4$ represents hydrogen, methyl or ethyl.

The present invention also provides a compound of formula IIB as depicted above, or a pharmaceutically acceptable salt thereof, wherein Q represents the residue of a cyclopropyl, cyclobutyl, cyclopentyl, cyclohexyl or phenyl ring; and Y, $R^1$, $R^3$ and $R^4$ are as defined above.

In relation to formula IIB above, $R^1$ suitably represents phenyl, fluorophenyl or difluorophenyl.

In a particular embodiment, Q suitably represents the residue of a cyclobutyl ring. In another embodiment, Q represents the residue of a cyclopentyl ring. In a further embodiment, Q represents the residue of a cyclohexyl ring. In a still further embodiment, Q represents the residue of a phenyl ring. In a yet further embodiment, Q represents the residue of a thienyl ring.

Suitably, $R^3$ represents hydrogen, fluoro or chloro, particularly hydrogen or chloro, especially hydrogen.

Suitably, $R^4$ represents methyl or ethyl, especially methyl.

Another subset of the compounds of formula IIA above is represented by the compounds of formula IIC, and pharmaceutically acceptable salts thereof:

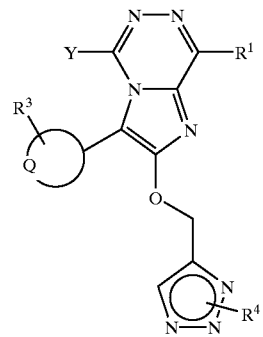

(IIC)

wherein
Y and $R^1$ are as defined with reference to formula I above; and
Q, $R^3$ and $R^4$ are as defined with reference to formula IIB above.

Specific compounds within the scope of the present invention include:
3,8-diphenyl-2-(2-methyl-2H-[1,2,4]triazol-3-ylmethoxy)imidazo[1,2-d][1,2,4]triazine;
8-(2-fluorophenyl)-2-(2-methyl-2H-[1,2,4]triazol-3-ylmethoxy)-3-phenyl-imidazo[1,2-d][1,2,4]triazine;
8-(2-fluorophenyl)-2-(1-methyl-1H-[1,2,4]triazol-3-ylmethoxy)-3-phenyl-imidazo[1,2-d][1,2,4]triazine;
8-(2,5-difluorophenyl)-2-(2-methyl-2H-[1,2,4]triazol-3-ylmethoxy)-3-phenylimidazo[1,2-d][1,2,4]triazine;
8-(4-fluorophenyl)-2-(2-methyl-2H-[1,2,4]triazol-3-ylmethoxy)-3-phenyl-imidazo[1,2-d][1,2,4]triazine;
8-(2,6-difluorophenyl)-2-(2-methyl-2H-[1,2,4]triazol-3-ylmethoxy)-3-phenylimidazo[1,2-d][1,2,4]triazine;
3-cyclobutyl-8-(2-fluorophenyl)-2-(2-methyl-2H-[1,2,4]triazol-3-ylmethoxy)-imidazo[1,2-d][1,2,4]triazine;
3-(3-chlorophenyl)-2-(2-methyl-2H-[1,2,4]triazol-3-ylmethoxy)-8-phenyl-imidazo[1,2-d][1,2,4]triazine;
3-cyclobutyl-5-methyl-2-(2-methyl-2H-[1,2,4]triazol-3-ylmethoxy)-8-phenylimidazo[1,2-d][1,2,4]triazine;
3-cyclopentyl-5-methyl-2-(2-methyl-2H-[1,2,4]triazol-3-ylmethoxy)-8-phenylimidazo[1,2-d][1,2,4]triazine;
8-(2-fluorophenyl)-5-methyl-2-(2-methyl-2H-[1,2,4]triazol-3-ylmethoxy)-3-phenylimidazo[1,2-d][1,2,4]triazine;
3-cyclopentyl-5-ethyl-2-(2-ethyl-2H-[1,2,4]triazol-3-ylmethoxy)-8-phenylimidazo[1,2-d][1,2,4]triazine;
3-cyclopentyl-5-ethyl-2-(2-methyl-2H-[1,2,4]triazol-3-ylmethoxy)-8-phenylimidazo[1,2-d][1,2,4]triazine;
3-cyclopentyl-5-cyclopropyl-2-(2-methyl-2H-[1,2,4]triazol-3-ylmethoxy)-8-phenylimidazo[1,2-d][1,2,4]triazine;

3-cyclopentyl-8-(2,6-difluorophenyl)-5-methyl-2-(2-methyl-2H-[1,2,4]triazol-3-ylmethoxy)imidazo[1,2-d][1,2,4]triazine;

3-cyclohexyl-8-(2-fluorophenyl)-5-methyl-2-(2-methyl-2H-[1,2,4]triazol-3-ylmethoxy)imidazo[1,2-d][1,2,4]triazine;

3,8-bis(2-fluorophenyl)-5-methyl-2-(2-methyl-2H-[1,2,4]triazol-3-ylmethoxy)imidazo[1,2-d][1,2,4]triazine;

3-cyclopentyl-8-(2,6-difluorophenyl)-2-(2-ethyl-2H-[1,2,4]triazol-3-ylmethoxy)-5-methylimidazo[1,2-d][1,2,4]triazine;

3-cyclopentyl-8-(2-fluorophenyl)-5-methyl-2-(3-methyl-3H-[1,2,3]triazol-4-ylmethoxy)imidazo[1,2-d][1,2,4]triazine;

3-cyclopentyl-8-(2-fluorophenyl)-5-methyl-2-(1-methyl-1H-[1,2,4]triazol-3-ylmethoxy)imidazo[1,2-d][1,2,4]triazine;

3-cyclopentyl-8-(2-fluorophenyl)-5-methyl-2-(1-methyl-1H-[1,2,3]triazol-4-ylmethoxy)imidazo[1,2-d][1,2,4]triazine;

3-cyclopentyl-2-(2-ethyl-2H-[1,2,4]triazol-3-ylmethoxy)-8-(2-fluorophenyl)-5-methylimidazo[1,2-d][1,2,4]triazine;

3-cyclopentyl-8-(2-fluorophenyl)-5-methyl-2-(2-methyl-2H-[1,2,4]triazol-3-ylmethoxy)imidazo[1,2-d][1,2,4]triazine;

3-cyclohexyl-2-(2-ethyl-2H-[1,2,4]triazol-3-ylmethoxy)-8-(2-fluorophenyl)-5-methylimidazo[1,2-d][1,2,4]triazine;

3-cyclopentyl-2-(2-ethyl-2H-[1,2,4]triazol-3-ylmethoxy)-5-methyl-8-phenyl-imidazo[1,2-d][1,2,4]triazine;

2-(2-ethyl-2H-[1,2,4]triazol-3-ylmethoxy)-5-methyl-8-phenyl-3-(thien-2-yl)-imidazo[1,2-d][1,2,4]triazine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof The binding affinity ($K_i$) of the compounds according to the present invention for the $\alpha 3$ subunit of the human $GABA_A$ receptor is conveniently as measured in the assay described hereinbelow. The $\alpha 3$ subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the $\alpha 3$ subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the $\alpha 1$ subunit of the human $GABA_A$ receptor.

The potentiation of the GABA $EC_{20}$ response in stably transfected cell lines expressing the $\alpha 3$ and $\alpha 1$ subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*; 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

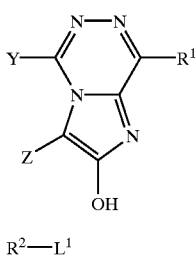

(III)

$R^2$—$L^1$ (IV)

wherein Y, Z, $R^1$ and $R^2$ are as defined above, and $L^1$ represents a suitable leaving group.

The leaving group $L^1$ is suitably a halogen atom, typically chloro.

The reaction between compounds III and IV is conveniently effected by stirring the reactants in a suitable solvent, typically N,N-dimethylformamide, in the presence of a base such as sodium hydride or potassium carbonate.

In another procedure, the compounds of formula I as defined above may be prepared by a process which comprises reacting a compound of formula III as defined above with a compound of formula V:

$R^2$—OH (V)

wherein $R^2$ is as defined above; in the presence of triphenylphosphine and diethyl azodicarboxylate.

The reaction is conveniently effected at a temperature in the region of 0° C., typically in an inert solvent such as tetrahydrofuran.

The intermediates of formula III above may be prepared by reacting a compound of formula VI with a compound of formula VII:

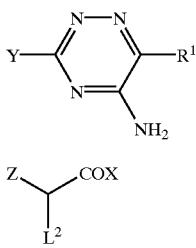

(VI)

(VII)

wherein Y, Z and $R^1$ are as defined above, $L^2$ represents a suitable leaving group, and X represents a halogen atom, preferably chloro.

The leaving group $L^2$ is suitably a halogen atom, e.g. chloro or bromo.

The reaction between compounds VI and VII may conveniently be accomplished by stirring the reactants in a solvent such as dichloromethane, typically in the presence of pyridine; followed by heating the product thereby obtained with sodium iodide and triethylamine in a solvent such as 1,2-dichloroethane or n-butanol. Alternatively, the reaction between compounds VI and VII may be effected by stirring at 0° C. in a suitable solvent, e.g. 1,2-dichloroethane, typically in the presence of approximately one equivalent of an organic base such as triethylamine; followed by heating at reflux in the presence of approximately one further equivalent of triethylamine.

In a further procedure, the compounds of formula I as defined above may be prepared by a process which comprises reacting a compound of formula VIII with a compound of formula IX:

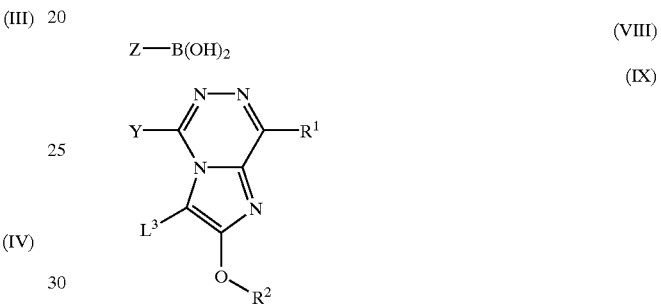

wherein Y, Z, $R^1$ and $R^2$ are as defined above, and $L^3$ represents a suitable leaving group; in the presence of a transition metal catalyst.

The leaving group $L^3$ is typically a halogen atom, e.g. bromo.

The transition metal catalyst of use in the reaction between compounds VIII and IX is suitably tris (dibenzylideneacetone)-dipalladium(0), in which case the reaction is conveniently effected at an elevated temperature in a solvent such as 1,4-dioxane, typically in the presence of tri-tert-butylphosphine and cesium carbonate.

The intermediates of formula IX in which the leaving group $L^3$ represents bromo may be prepared by brominating a compound of formula X:

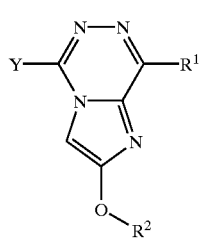

(X)

wherein Y, $R^1$ and $R^2$ are as defined above.

The bromination reaction is conveniently effected by treating the appropriate compound of formula X with bromine in a suitable solvent, e.g. a mixture of carbon tetrachloride and chloroform.

The intermediates of formula X may be prepared by reacting a compound of formula IV as defined above with a compound of formula XI:

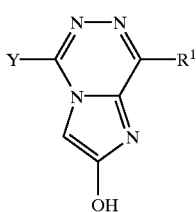

wherein Y and $R^1$ are as defined above; under conditions analogous to those described above for the reaction between compounds III and IV.

Alternatively, the intermediates of formula X may be prepared by reacting a compound of formula V as defined above with a compound of formula XI as defined above in the presence of triphenylphosphine and diethyl azodicarboxylate; under conditions analogous to those described above for the reaction between compounds III and V.

The intermediates of formula XI may be prepared by reacting a compound of formula VI as defined above with a compound of formula XII:

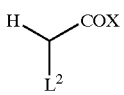

wherein $L^2$ and X are as defined above; under conditions analogous to those described above for the reaction between compounds VI and VII.

The intermediates of formula IV and V above may be prepared by the procedures described in WO 98/04559, or by methods analogous thereto.

Where they are not commercially available, the starting materials of formula VI, VII, VIII and XII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-diethylformamide, or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-(di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [3H]-flumazenil from the α2 and/or α3 subunit of the human GABA$_A$ receptor of 100 nM or less.

EXAMPLE 1

3,8-Diphenyl-2-(2-methyl-2H-[1,2,4]triazol-3-ylmethoxy)imidazo[1,2-d][1,2,4]triazine a) Hydrazono-phenyl-acetaldehyde Oxime A solution of 2-isonitrosoacetophenone (50 g, 335 mmol) in methanol (500 ml) was treated with hydrazine monohydrate (19.5 ml, 402 mmol). The reaction mixture was stirred at room temperature for 20 h at which time the methanol was evaporated in vacuo. The residue was purified by flash chromatography (SiO$_2$; 20% EtOAc in hexanes) to afford 37 g (227 mmol; 68%) of hydrazono-phenyl-acetaldehyde oxime as a white solid. $\delta_H$ (360 MHz; CDCl$_3$) 7.22–7.42 (3H, m, aromatics), 7.42–7.60 (2H, m, aromatics), 7.99 (2H, br s, NH$_2$), 8.26 (2H, br s, ArC(NNH$_2$)CHNOH); m/z (ES$^+$) 164 (M$^+$+H, 100%).

b) 6-Phenyl-[1,2,4]triazine-4-oxide

To a mixture of hydrazono-phenyl-acetaldehyde oxime (30 g, 184 mmol) and triethyl orthoformate (30.6 ml, 184 mmol) was added 4-toluenesulphonic acid monohydrate (3.5 g, 18.4 mmol). The reaction mixture was heated at 110° C. with stirring for 30 min. The cooled reaction mixture was recrystallised from CH$_2$Cl$_2$/hexane to give 27 g (156 mmol, 85%) of 6-phenyl-[1,2,4]triazine-4-oxide as a pale yellow solid. $\delta_H$ (400 MHz; CDCl$_3$) 7.55–7.63 (3H, m, aromatics), 8.01 (2H, dd, J 8.1 and 1.7, aromatics), 8.52 (1H, d, J 1.7, triazine H5), 9.27 (1H, d, J 1.7, triazine H3); m/z (ES$^+$) 174 (M$^+$+H, 100%).

c) 6-Phenyl-[1,2,4]triazine

A mixture of 6-phenyl-[1,2,4]triazine-4-oxide (27 g, 156 mmol) and triethyl phosphite (500 ml) was heated under reflux for 30 min. The cooled reaction mixture was evaporated tit vacuo and the residue was purified by flash chromatography (SiO$_2$; 50% Et$_2$O in hexanes) to afford 19 g (121 mmol, 78%) of 6-phenyl-[1,2,4]triazine as a yellow solid. $\delta_H$ (400 MHz; CDCl$_3$) 7.56–7.59 (3H, m, aromatics), 8.10–8.14 (2H, m, aromatics), 9.03 (1H, s, triazine H5), 9.65 (1H, s, triazine H3); m/z (ES$^+$) 158 (M$^+$+H, 100%).

d) 6-Phenyl-[1,2,4]triazin-5-ylamine

To a mixture of 6-phenyl-[1,2,4]triazine (18 g, 115 mmol) in anhydrous liquid ammonia (1 l) under an atmosphere of nitrogen at −37° C. was added in one portion potassium permanganate (22.6 g, 143 mmol). The reaction mixture was stirred at −37° C. for 30 min and then the ammonia evaporated. To the residue was added propan-2-ol (800 ml) and the resulting mixture heated under reflux for 10 min, then filtered through hyflo. The filtrate was evaporated in vacuo. The residue was purified by flash chromatography (SiO$_2$; 4% MeOH in CH$_2$Cl$_2$+0.5% NH$_3$) to afford 9.8 g (57 mmol, 50%) of 6-phenyl-[1,2,4]triazin-5-ylamine as a yellow solid. $\delta_H$ (360 MHz; CDCl$_3$) 5.58 (2H, br s, NH$_2$), 7.51–7.57 (3H, m, aromatics), 7.68–7.72 (2H, m, aromatics), 8.80 (1H, s, triazine H3); m/z (ES$^+$) 173 (M$^+$+H, 100%).

e) 3,8-Diphenylimidazo[1,2-d][1,2,4]triazin-2-ol

To a solution of 6-phenyl-[1,2,4]triazin-5-ylamine (1.1 g, 6.4 mmol) and triethylamine (891 μl, 6.4 mmol) in anhydrous 1,2-dichloroethane (75 ml) under an atmosphere of nitrogen was added dropwise 2-chloro-2-phenylacetyl chloride (1.01 ml, 6.4 mmol). The reaction mixture was stirred at 0° C. for 90 min, then triethylamine (891 μl, 6.4 mmol) was added, and the resulting mixture heated under reflux for 30 min. The cooled reaction mixture was partitioned between CH$_2$Cl$_2$ (100 ml) and water (100 ml). The organic layer was separated, dried over MgSO$_4$ and evaporated in vacuo. The solid residue was triturated with a 1:1 mixture of CH$_2$Cl$_2$ and MeOH (10 ml), filtered and dried to give 780 mg (2.7 mmol, 42%) of 3,8-diphenylimidazo[1,2-d][1,2,4]triazin-2-ol as a pale yellow solid. $\delta_H$ (360 MHz; DMSO-d$_6$) 7.41 (1H, t, J 7.3 and 7.2, aromatic), 7.50–7.63 (5H, m, aromatics), 7.82 (2H, d, J 7.8, aromatics), 8.57 (2H, m, aromatics), 9.65 (1H, s, imidazotriazine H5), 11.72 (1H, br s, OH); m/z (ES$^+$) 289 (M$^+$+H, 100%).

f) 3,8-Diphenyl-2-(2-methyl-2H-[1,2,4]triazol-3-ylmethoxy)imidazo[1,2-d][1,2,4]triazine To a solution of 3,8-diphenylimidazo[1,2-d][1,2,4]triazin-2-ol (500 mg, 1.74 mmol) and 3-chloromethyl-2-methyl-2H-[1,2,4]triazole hydrochloride (320 mg, 1.91 mmol) in anhydrous N,N-dimethylformamide under an atmosphere of nitrogen was added sodium hydride (153 mg of a 60% dispersion in oil, 3.8 mmol). The reaction mixture was stirred at room temperature for 72 h. The mixture was partitioned between EtOAc (80 ml) and water (150 ml), the organic layer was separated, and the aqueous layer extracted with a further two portions of EtOAc (80 ml). The combined EtOAc layers were washed with saturated NaCl solution (100 ml), separated, dried over MgSO$_4$ and evaporated in vacuo. The residue was purified by flash chromatography (SiO$_2$; 2% MeOH in CH$_2$Cl$_2$+0.5% NH$_3$), and the product recrystallised from CH$_2$Cl$_2$ to afford 235 mg (0.6 mmol, 35%) as a white solid. (Found: C, 63.66; H, 4.23; N, 24.54; C$_{21}$H$_{17}$N$_7$O.0.5H$_2$O.0.07CH$_2$Cl$_2$ requires C, 63.47; H, 4.59; N, 24.59%); m.p. 179° C. (from CH$_2$Cl$_2$); $\delta_H$ (400 MHz; CDCl$_3$) 3.95 (3H, s, NCH$_3$), 5.75 (2H, s, OCH$_2$), 7.46 (1H, t, J 7.3, aromatic), 7.52–7.60 (5H, m, aromatics), 7.63 (2H, d, J 7.6, aromatics), 7.88 (1H, s, triazole H5), 8.57–8.65 (2H, br m, aromatics), 9.43 (1H, s, imidazotriazine H5); m/z (ES$^+$) 384 (M$^+$+H, 100%).

EXAMPLE 2

8-(2-Fluorophenyl)-2-(2-methyl-2H-[1,2,4]triazol-3-ylmethoxy)-3-phenyl-imidazo[1,2-d][1,2,4]triazine By substantially following the procedures of Example 1, utilising hydrazono-(2-fluorophenyl)-acetaldehyde oxime in place of hydrazono-phenyl-acetaldehyde oxime, was prepared the title compound as a white solid. (Found: C, 61.32; H, 3.82; N, 23.80; C$_{21}$H$_{16}$FN$_7$O.2.2% ash requires C, 61.43; H, 3.93; N, 23.89%); m.p. 195° C. (from CH$_2$Cl$_2$); $\delta_H$ (400 MHz; CDCl$_3$) 3.88 (3H, s, NCH$_3$), 5.64 (2H, s, OCH$_2$), 7.29 (1H, m, aromatic), 7.37 (1H, t, J 7.6, aromatic), 7.46 (1H, t, J 7.5 and 7.2, aromatic), 7.52–7.61 (3H, m, aromatics), 7.65 (2H, d, J 7.9, aromatics), 7.84 (2H, m, aromatics), 9.49 (1H, s, imidazotriazine H5); m/z (ES$^+$) 402 (M$^+$+H, 100%).

EXAMPLE 3

8-(2-Fluorophenyl)-2-(1-methyl-1H-[1,2,4]triazol-3-ylmethoxy)-3-phenyl-imidazo[1,2-d][1,2,4]triazine By substantially following the procedures of Example 1, utilising hydrazono-(2-fluorophenyl)-acetaldehyde oxime in place of hydrazono-phenyl-acetaldehyde oxime, and 3-chloromethyl-1-methyl-1H-[1,2,4]triazole in place of 3-chloromethyl-2-methyl-2H-[1,2,4]triazole, was prepared the title compound as a white solid. (Found: C, 61.88; H, 3.81; N, 23.93; C$_{21}$H$_{16}$FN$_7$O.1.7% ash requires C, 61.78; H, 3.95; N, 24.01%); m.p. 186° C. (from CH$_2$Cl$_2$/hexane); $\delta_H$ (400 MHz; CDCl$_3$) 3.91 (3H, s, NCH$_3$), 5.63 (2H, s, OCH$_2$), 7.27 (1H, m, aromatic), 7.34 (1H, t, J 7.6, aromatic), 7.42 (1H, t, J 7.4, aromatic), 7.51–7.58 (3H, m, aromatics), 7.70 (2H, d, J 7.8, aromatics), 7.93 (1H, t, J 7.4, aromatic), 8.00 (1H, s, triazole H5), 9.50 (1H, s, imidazotriazine H5); m/z (ES$^+$) 402 (M$^+$+H, 100%).

EXAMPLE 4

8-(2,5-Difluorophenyl)-2-(2-methyl-2H-[1,2,4]triazol-3-ylmethoxy)-3-phenylimidazo[1,2-d][1,2,4]triazine By substantially following the procedures of Example 1, utilising hydrazono-(2,5-difluorophenyl)-acetaldehyde oxime in place of hydrazono-phenyl-acetaldehyde oxime, was prepared the title compound as a white solid. (Found: C, 58.29; H, 3.45; N, 22.58; $C_{21}H_{15}F_2N_7O.3.25\%$ ash requires C, 58.23; H, 3.49; N, 22.63%); m.p. 200° C. (from $CH_2Cl_2$/hexane); $\delta_H$ (400 MHz; $CDCl_3$) 3.91 (3H, s, $NCH_3$), 5.65 (2H, s, $OCH_2$), 7.21–7.31 (2H, m, aromatics), 7.47 (1H, t, J 7.4, aromatic), 7.53–7.67 (5H, m, aromatics), 7.86 (1H, s, triazole H5), 9.50 (1H, s, imidazotriazine H5); m/z ($ES^+$) 420 ($M^+$+H, 100%).

EXAMPLE 5

8-(4-Fluorophenyl)-2-(2-methyl-2H-[1,2,4]triazol-3-ylmethoxy)-3-phenyl-imidazo[1,2-d][1,2,4]triazine By substantially following the procedures of Example 1, utilising hydrazono-(4-fluorophenyl)-acetaldehyde oxime in place of hydrazono-phenyl-acetaldehyde oxime, was prepared the title compound as a white solid. (Found: C, 56.11; H, 3.72; N, 21.12; $C_{21}H_{16}FN_7O.0.75CH_2Cl_2$ requires C, 56.17; H, 3.79; N, 21.08%); m.p. 130° C. (from $CH_2Cl_2$); $\delta_H$ (360 MHz; $CDCl_3$) 3.95 (3H, s, $NCH_3$), 5.75 (2H, s, $OCH_2$), 7.25–7.30 (2H, m, aromatics), 7.45–7.50 (1H, m, aromatic), 7.57 (2H, t, J 7.8 and 7.4 aromatics), 7.62 (2H, dd, J 8.6 and 1.5, aromatics), 8.71 (2H, m, aromatics), 9.43 (1H, s, imidazotriazine H5); m/z ($ES^+$) 402 ($M^+$+H, 100%).

EXAMPLE 6

8-(2,6-Difluorophenyl)-2-(2-methyl-2H-[1,2,4]triazol-3-ylmethoxy)-3-phenylimidazo[1,2-d][1,2,4]triazine By substantially following the procedures of Example 1, utilising hydrazono-(2,6-difluorophenyl)-acetaldehyde oxime in place of hydrazono-phenyl-acetaldehyde oxime, was prepared the title compound as a white solid. (Found: C, 59.67; H, 3.29; N, 23.28; $C_{21}H_{15}F_2N_7O.0.1H_2O$ requires C, 59.88; H, 3.64; N, 23.29%); m.p. 190° C. (from $CH_2Cl_2$/hexane); $\delta_H$ (400 MHz; $CDCl_3$) 3.85 (3H, s, $NCH_3$), 5.60 (2H, s, $OCH_2$), 7.13 (2H, t, J 8.0, aromatics), 7.47 (1H, t, J 7.4, aromatic), 7.53–7.59 (3H, m, aromatics), 7.65 (2H, d, J 7.6, aromatics), 7.85 (1H, s, triazole H5), 9.52 (1H, s, imidazotriazine H5); m/z ($ES^+$) 420 ($M^+$+H, 100%).

EXAMPLE 7

3-Cyclobutyl-8-(2-fluorophenyl)-2-(2-methyl-2H-[1,2,4]triazol-3-ylmethoxy)imidazo[1,2-d][1,2,4]triazine By substantially following the procedures of Example 1, utilising hydrazono-(2-fluorophenyl)-acetaldehyde oxime in place of hydrazono-phenyl-acetaldehyde oxime, and 2-bromo-2-cyclobutylacetyl chloride (prepared from cyclobutylacetyl chloride by the method of Gleason, *Tetrahedron Lett.*, 1970, 39, 3431) in place of 2-chloro-2-phenylacetyl chloride, was prepared the title compound as a white solid. (Found: C, 58.99; H, 4.47; N, 25.20; $C_{19}H_{18}FN_7O.2\%$ ash requires C, 58.90; H, 4.68; N, 25.31%); m.p. 120° C. (from $CH_2Cl_2$/hexane); $\delta_H$ (360 MHz; $CDCl_3$) 1.96–2.07 (1H, m, aliphatic), 2.10–2.24 (1H, m, aliphatic), 2.40–2.53 (2H, m, aliphatics), 2.53–2.65 (2H, m, aliphatics), 3.77–3.86 (1H, m, aliphatic), 3.91 (3H, s, $NCH_3$), 5.57 (2H, s, $OCH_2$), 7.26 (1H, m, aromatic), 7.34 (1H, m, aromatic), 7.51–7.59 (1H, m, aromatic), 7.79 (1H, m, aromatic), 7.86 (1H, s, triazole H5), 9.10 (1H, s, imidazotriazine H5); m/z ($ES^+$) 380 ($M^+$+H, 100%).

EXAMPLE 8

3-(3-Chlorophenyl)-2-(2-methyl-2H-[1,2,4]triazol-3-ylmethoxy)-8-phenyl-imidazo[1,2-d][1,2,4]triazine By substantially following the procedures of Example 1, utilising 2-chloro-2-(3-chlorophenyl)acetyl chloride in place of 2-chloro-2-phenylacetyl chloride, was prepared the title compound as a white solid. (Found: C, 59.56; H, 3.72; N, 23.26; $C_{21}H_{16}ClN_7O.0.25H_2O$ requires C, 59.72; H, 3.94; N, 23.21%); m.p. 80–84° C.; $^1$H NMR (400 MHz, DMSO-$d_6$) 3.93 (3H, s), 5.76 (2H, s), 7.52–7.56 (1H, m), 7.58–7.65 (4H, m), 7.75–7.78 (1H, m), 7.84–7.86 (1H, m), 7.93 (1H, s), 8.51–8.57 (2H, m), 9.73 (1H, s); m/z ($ES^+$) 418 (M+1).

EXAMPLE 9

3-Cyclobutyl-5-methyl-2-(2-methyl-2H-[1,2,4]triazol-3-ylmethoxy)-8-phenylimidazo[1,2-d][1,2,4]triazine By substantially following the procedures of Example 1, utilising trimethyl orthoacetate in place of triethyl orthoformate, and 2-bromo-2-cyclobutylacetyl chloride in place of 2-chloro-2-phenylacetyl chloride, was prepared the title compound as a white solid. (Found: C, 63.19; H, 5,41; N, 25.40; $C_{20}H_{21}N_7O.0.3H_2O$ requires C, 63.08; H, 5.72; N, 25.75%); m.p. 160° C. (from $CH_2Cl_2$/hexane); $\delta_H$ (400 MHz; $CDCl_3$) 1.88–2.06 (2H, m, aliphatic), 2.27–2.39 (2H, m, aliphatic), 2.67–2.80 (2H, m, aliphatics), 3.06 (3H, s, imidazotriazine $CH_3$), 3.98 (3H, s, $NCH_3$), 4.07 (1H, m, aliphatic), 5.67 (2H, s, $OCH_2$), 7.53 (3H, m, aromatics), 7.90 (1H, s, triazole H5), 8.48 (2H, m, aromatics); m/z ($ES^+$) 376 ($M^+$+H, 100%).

EXAMPLE 10

3-Cyclopentyl-5-methyl-2-(2-methyl-2H-[1,2,4]triazol-3-ylmethoxy)-8-phenylimidazo[1,2-d][1,2,4]triazine By substantially following the procedures of Example 1, utilising trimethyl orthoacetate in place of triethyl orthoformate, and 2-bromo-2-cyclopentylacetyl chloride in place of 2-chloro-2-phenylacetyl chloride, was prepared the title compound as a white solid. (Found: C, 65.08; H, 5.78; N, 25.44; $C_{21}H_{23}N_7O$ requires C, 64.76; H, 5.95; N, 25.17%); m.p. 137° C. (from $CH_2Cl_2$/hexane); $\delta_H$ (360 MHz; $CDCl_3$) 1.61–1.75 (2H, m, aliphatics), 1.77–1.91 (2H, m, aliphatics), 1.94–2.11 (4H, m, aliphatics), 3.09 (3H, s, imidazotriazine $CH_3$), 3.71 (1H, quintet, J 8.6, aliphatic), 3.95 (3H, s, $NCH_3$), 5.64 (2H, s, $OCH_2$), 7.50–7.54 (3H, m, aromatics), 7.89 (1H, s, triazole H5), 8.46–8.49 (2H, m, aromatics); m/z ($ES^+$) 390 ($M^+$+H, 100%).

EXAMPLE 11

8-(2-Fluorophenyl)-5-methyl-2-(2-methyl-2H-[1,2,4]triazol-3-ylmethoxy)-3-phenylimidazo[1,2-d][1,2,4]triazine By substantially following the procedures of Example 1, utilising 5-amino-6-(2-fluorophenyl)-3-methyl-[1,2,4]

triazine (prepared by the method of Uchytilova, *Collect. Czech. Chem. Commun.*, 1972, 37, 2221–2226) in place of 6-phenyl-[1,2,4]triazin-5-ylamine, was prepared the title compound as a white foam. $\delta_H$ (360 MHz; CDCl$_3$) 2.48 (3H, s, imidazotriazine CH$_3$), 3.77 (3H, s, NCH$_3$), 5.53 (2H, s, OCH$_2$), 7.24–7.31 (1H, m, aromatic), 7.33–7.38 (1H, m, aromatic), 7.40–7.44 (2H, m, aromatics), 7.46–7.60 (4H, m, aromatics), 7.78–7.83 (2H, m, aromatics); m/z (ES$^+$) 416 (M$^+$+H, 100%).

EXAMPLE 12

3-Cyclopentyl-5-ethyl-2-(2-ethyl-2H-[1,2,4]triazol-3-ylmethoxy)-8-phenylimidazo[1,2-d][1,2,4]triazine a) 3-Cyclopentyl-5-ethyl-8-phenylimidazo[1,2-d][1,2,4]triazin-2-ol By substantially following the procedures of Example 1, utilising trimethyl orthopropionate in place of triethyl orthoformate, and 2-bromo-2-cyclopentylacetyl chloride in place of 2-chloro-2-phenylacetyl chloride, was prepared the title compound as a tan solid. m/z (ES$^+$) 309 (M$^+$+H, 100%).

b) 3-Cyclopentyl-5-ethyl-2-(2-ethyl-2H-[1,2,4]triazol-3-ylmethoxy)-8-phenylimidazo[1,2-d][1,2,4]triazine To a solution of the product of Example 12 a) (150 mg, 0.48 mmol) and (2-ethyl-2H-[1,2,4]triazol-3-yl)methanol (93 mg, 0.73 mmol) in tetrahydrofuran (5 ml) at 0° C. was added triphenylphosphine (192 mg, 0.73 mmol) followed by diethyl azodicarboxylate (110 μl, 0.73 mmol) dropwise with stirring. After 2 hours the tetrahydrofuran was evaporated in vacuo and the residue dissolved in dichloromethane (50 ml) and washed with water (2×20 ml). The organic phase was separated, dried over MgSO$_4$, filtered and evaporated in vacuo. The crude product was purified by prep. TLC (SiO$_2$; 30% ethyl acetate in isohexane), and the product recrystallised from ether/isohexane to afford 35 mg (17%) as a white solid. $\delta_H$ (400 MHz; CDCl$_3$) 1.43 (3H, t, J 7.2), 1.57 (3H, t, J 7.2), 1.71 (2H, m), 1.84 (2H, m), 2.02 (4H, m), 3.37 (2H, q, J 7.3), 3.66 (1H, quin, J 8.7), 4.30 (2H, q, J 7.2), 5.66 (2H, s), 7.53 (3H, m), 7.92 (1H, s), 8.54 (2H, m); m/z (ES$^+$) 418 (M$^+$+H, 100%).

EXAMPLE 13

3-Cyclopentyl-5-ethyl-2-(2-methyl-2H-[1,2,4]triazol-3-ylmethoxy)-8-phenylimidazo[1,2-d][1,2,4]triazine By substantially following the procedures of Example 12, utilising (2-methyl-2H-[1,2,4]triazol-3-yl)methanol in place of (2-ethyl-2H-[1,2,4]triazol-3-yl)methanol, and resin bound triphenylphosphine, was prepared the title compound as a white solid. $\delta_H$ (360 MHz; CDCl$_3$) 1.57 (3H, t, J 7.3), 1.69 (2H, m), 1.86 (2H, m), 2.02 (4H, m), 3.38 (2H, q, J 7.3), 3.67 (1H, quin, J 8.7), 4.30 (2H, q, J 7.2), 5.65 (2H, s), 7.53 (3H, m), 7.89 (1H, s), 8.50 (2H, m); m/z (ES$^+$) 404 (M$^+$+H, 100%).

EXAMPLE 14

3-Cyclopentyl-5-cyclopropyl-2-(2-methyl-2H-[1,2,4]triazol-3-ylmethoxy)-8-phenylimidazo[1,2-d][1,2,4]triazine By substantially following the procedures of Example 12, utilising cyclopropane carboxylic acid trimethyl ester (prepared from cyclopropyl cyanide by the method of Ueno, *J. Med. Chem.*, 1991, 34, 2468) in place of triethyl orthopropionate, and (2-methyl-2H-[1,2,4]triazol-3-yl)methanol in place of (2-ethyl-2H-[1,2,4]triazol-3-yl)methanol, and resin bound triphenylphosphine, was prepared the title compound as a white solid. $\delta_H$ (400 MHz; CDCl$_3$) 1.21 (2H, m), 1.58 (2H, m), 1.68 (2H, m), 1.86 (2H, m), 2.03 (4H, m), 2.46 (1H, m), 3.97 (3H, s), 3.67 (1H, quintet, J 8.6), 5.65 (2H, s), 7.53 (3H, m), 7.90 (1H, s), 8.50 (2H, m); m/z (ES$^+$) 416 (M$^+$+H, 100%).

EXAMPLE 15

3-Cyclopentyl-8-(2,6-difluorophenyl)-5-methyl-2-(2-methyl-2H-[1,2,4]triazol-3-ylmethoxy)imidazo[1,2-d][1,2,4]triazine By substantially following the procedures of Example 25, utilising hydrazono-(2,6-difluorophenyl)-acetaldehyde oxime in place of hydrazono-phenyl-acetaldehyde oxime in step a), using 1,2-dichloroethane in place of n-butanol in step c), and in step d) using 3-chloromethyl-2-methyl-2H-[1,2,4]triazole hydrochloride in place of 3-chloromethyl-2-ethyl-2H-[1,2,4]triazole hydrochloride, was prepared the title compound as a tan solid. $\delta_H$ (360 MHz; CDCl$_3$) 1.68 (3H, m), 1.81 (2H, m), 2.03 (3H, m), 3.12 (3H, s), 3.69 (1H, quintet, J 8.5), 3.81 (3H, s), 5.49 (2H, s), 7.08 (2H, m), 7.48 (1H, m), 7.84 (1H, s); m/z (ES$^+$) 426 (M$^+$+H, 100%).

EXAMPLE 16

3-Cyclohexyl-8-(2-fluorophenyl)-5-methyl-2-(2-methyl-2H-[1,2,4]triazol-3-ylmethoxy)imidazo[1,2-d][1,2,4]triazine By substantially following the procedures of Example 25, utilising hydrazono-(2-fluorophenyl)-acetaldehyde oxime in place of hydrazono-phenyl-acetaldehyde oxime in step a), using 2-bromo-2-cyclohexylacetyl chloride in place of 2-bromo-2-cyclopentylacetyl chloride and 1,2-dichloroethane in place of n-butanol in step c), and using 3-chloromethyl-2-methyl-2H-[1,2,4]triazole hydrochloride in place of 3-chloromethyl-2-ethyl-2H-[1,2,4]triazole hydrochloride in step d), was prepared the title compound as a white solid. $\delta_H$ (360 MHz; CDCl$_3$) 1.31 (2H, m), 1.69 (3H, m), 1.87 (5H, m), 3.10 (3H, s), 3.30 (1H, m), 3.84 (3H, s), 5.52 (2H, s), 7.24 (1H, m), 7.32 (1H, m), 7.54 (1H, m), 7.71 (1H, m), 7.85 (1H, s); m/z (ES$^+$) 422 (M$^+$+H, 100%).

EXAMPLE 17

3,8-bis(2-Fluorophenyl)-5-methyl-2-(2-methyl-2H-[1,2,4]triazol-3-ylmethoxy)imidazo[1,2-d][1,2,4]triazine By substantially following the procedures of Example 25, utilising hydrazono-(2-fluorophenyl)-acetaldehyde oxime in place of hydrazono-phenyl-acetaldehyde oxime in step a), using 2-bromo-2-(2-fluorophenyl)acetyl chloride in place of 2-bromo-2-cyclopentylacetyl chloride and 1,2-dichloroethane in place of n-butanol in step c), and using 3-chloromethyl-2-methyl-2H-[1,2,4]triazole hydrochloride in place of 3-chloromethyl-2-ethyl-2H-[1,2,4]triazole hydrochloride in step d), was prepared the title compound as a tan solid. $\delta_H$ (360 MHz; CDCl$_3$) 2.55 (3H, s), 3.80 (3H, s), 5.55 (2H, dd, J 13.1 and 14.2), 7.21–7.57 (7H, m), 7.82 (2H, t, J 7.6); m/z (ES$^+$) 434 (M$^+$+H, 100%).

EXAMPLE 18

3-Cyclopentyl-8-(2,6-difluorophenyl)-2-(2-ethyl-2H-[1,2,4]triazol-3-ylmethoxy)-5-methylimidazo[1,2-d][1,2,4]triazine By substantially following the procedures of Example 15, utilising 3-chloromethyl-2-ethyl-2H-[1,2,4]triazole hydrochloride in place of 3-chloromethyl-2-methyl-2H-[1,2,4]triazole hydrochloride, was prepared the title compound as a tan solid. $\delta_H$ (360 MHz; CDCl$_3$) 1.34 (3H, t, J 7.3), 1.65–2.07 (8H, m), 3.12 (3H, s), 3.69 (1H, quintet, J 8.6), 4.18 (2H, q, J 7.2), 5.52 (2H, s), 7.08 (2H, m), 7.49 (1H, m), 7.87 (1H, s); m/z (ES$^+$) 440 (M$^+$+H, 100%).

EXAMPLE 19

3-Cyclopentyl-8-(2-fluorophenyl)-5-methyl-2-(3-methyl-3H-[1,2,3]triazol-4-ylmethoxy)imidazo[1,2-d][1,2,4]triazine By substantially following the procedures of Example 15, utilising hydrazono-(2-fluorophenyl)-acetaldehyde oxime in place of hydrazono-(2,6-difluorophenyl)-acetaldehyde oxime, and 4-chloromethyl-3-methyl-3H-[1,2,3]triazole hydrochloride in place of 3-chloromethyl-2-methyl-2H-[1,2,4]triazole, was prepared the title compound as a white solid. $\delta_H$ (400 MHz; CDCl$_3$) 1.63 (2H, m), 1.86 (2H, m), 1.96 (2H, m), 2.08 (2H, m), 3.10 (3H, s), 3.70 (1H, quintet, J 7.7), 3.91 (3H, s), 5.50 (2H, s), 7.20–7.31 (2H, m), 7.48 (1H, m), 7.81 (1H, m), 8.00 (1H, s); m/z (ES$^+$) 408 (M$^+$+H, 100%).

EXAMPLE 20

3-Cyclopentyl-8-(2-fluorophenyl)-5-methyl-2-(1-methyl-1H-[1,2,4]triazol-3-ylmethoxy)imidazo[1,2-d][1,2,4]triazine By substantially following the procedures of Example 15, utilising hydrazono-(2-fluorophenyl)-acetaldehyde oxime in place of hydrazono-(2,6-difluorophenyl)-acetaldehyde oxime, and 3-chloromethyl-1-methyl-1H-[1,2,4]triazole hydrochloride in place of 3-chloromethyl-2-methyl-2H-[1,2,4]triazole hydrochloride, was prepared the title compound as a white solid. $\delta_H$ (400 MHz; CDCl$_3$) 1.70 (2H, m), 1.85 (2H, m), 1.97 (4H, m), 3.10 (3H, s), 3.70 (1H, quintet, J 8.6), 4.04 (3H, s), 5.50 (2H, s), 7.26 (1H, m), 7.34 (1H, m), 7.53 (1H, m), 7.73 (2H, m); m/z (ES$^+$) 408 (M$^+$+H, 100%).

EXAMPLE 21

3-Cyclopentyl-8-(2-fluorophenyl)-5-methyl-2-(1-methyl-1H-[1,2,3]triazol-4-ylmethoxy)imidazo[1,2-d][1,2,4]triazine By substantially following the procedures of Example 15, utilising hydrazono-(2-fluorophenyl)-acetaldehyde oxime in place of hydrazono-(2,6-difluorophenyl)-acetaldehyde oxime, and 4-chloromethyl-1-methyl-1H-[1,2,3]triazole hydrochloride in place of 3-chloromethyl-2-methyl-2H-[1,2,4]triazole hydrochloride, was prepared the title compound as a white solid. $\delta_H$ (360 MHz; CDCl$_3$) 1.65 (4H, m), 1.90 (3H, m), 2.01 (1H, m), 3.09 (3H, s), 3.67 (1H, quintet, J 8.5), 5.53 (2H, s), 7.26 (1H, m), 7.34 (1H, m), 7.55 (1H, m), 7.63 (1H, s), 7.77 (1H, m); m/z (ES$^+$) 408 (M$^+$+H, 100%).

EXAMPLE 22

3-Cyclopentyl-2-(2-ethyl-2H-[1,2,4]triazol-3-ylmethoxy)-8-(2-fluoro-phenyl)-5-methylimidazo[1,2-d][1,2,4]triazine By substantially following the procedures of Example 18, utilising hydrazono-(2-fluorophenyl)-acetaldehyde oxime in place of hydrazono-(2,6-difluorophenyl)-acetaldehyde oxime, was prepared the title compound as a white solid. $\delta_H$ (360 MHz; CDCl$_3$) 1.34 (3H, t, J 7.3), 1.68 (2H, m), 1.85 (2H, m), 1.95–2.01 (4H, m), 3.11 (3H, s), 3.69 (1H, quintet, J 8.5), 4.21 (2H, q, J 7.3), 5.55 (2H, s), 7.21 (1H, m), 7.32 (1H, m), 7.50–7.56 (1H, m), 7.71–7.76 (1H, m), 7.87 (1H, s); m/z (ES$^+$) 422 (M$^+$+H, 100%).

EXAMPLE 23

3-Cyclopentyl-8-(2-fluorophenyl)-5-methyl-2-(2-methyl-2H-[1,2,4]triazol-3-ylmethoxy)imidazo[1,2-d][1,2,4]triazine By substantially following the procedures of Example 20, utilising 3-chloromethyl-2-methyl-2H-[1,2,4]triazole hydrochloride in place of 3-chloromethyl-1-methyl-1H-[1,2,4]triazole hydrochloride, was prepared the title compound as a white solid. $\delta_H$ (360 MHz; CDCl$_3$) 1.68 (2H, m), 1.86 (2H, m), 1.99–2.09 (4H, m), 3.11 (3H, s), 3.70 (1H, quintet, J 8.5), 3.83 (3H, s), 5.23 (2H, s), 7.21–7.23 (1H, m), 7.30–7.34 (1H, m), 7.50–7.54 (1H, m), 7.69–7.74 (1H, m), 7.84 (1H, s); m/z (ES$^+$) 408 (M$^+$+H, 100%).

EXAMPLE 24

3-Cyclohexyl-2-(2-ethyl-2H-[1,2,4]triazol-3-ylmethoxy)-8-(2-fluorophenyl)-5-methylimidazo[1,2-d][1,2,4]triazine By substantially following the procedures of Example 16, utilising 3-chloromethyl-2-ethyl-2H-[1,2,4]triazole hydrochloride in place of 3-chloromethyl-2-methyl-2H-[1,2,4]triazole hydrochloride, was prepared the title compound as a white solid. $\delta_H$ (360 MHz; CDCl$_3$) 1.19–1.37 (6H, m), 1.73–1.94 (7H, m), 3.11 (3H, s), 3.45–3.51 (1H, m), 4.19–4.25 (2H, q, J 6.8 and 7.1), 5.55 (2H, s), 7.21–7.34 (2H, m), 7.53–7.54 (1H, m), 7.73–7.75 (1H, m), 7.89 (1H, s); m/z (ES$^+$) 436 (M$^+$+H, 100%).

EXAMPLE 25

3-Cyclopentyl-2-(2-ethyl-2H-[1,2,4]triazol-3-ylmethoxy)-5-methyl-8-phenyl-imidazo[1,2-d][1,2,4]triazine a) 3-Methyl-6-phenyl-[1,2,4]triazine-4-oxide To a solution of hydrazono-phenyl-acetaldehyde oxime (28 g, 168 mmol) at room temperature under nitrogen in dichloromethane (300 ml) was added trimethyl orthoacetate (19 ml, 168 mmol) and p-toluenesulfonic acid (1.6 g, 8.4 mmol). The reaction mixture was stirred for 18 h and then concentrated in vacuo. Xylene (300 ml) was added followed by trimethyl orthoacetate (19 ml, 168 mmol) and the mixture heated to 130° C. for 2 h. The reaction mixture was evaporated in vacuo. The residue was purified by flash chromatography (SiO$_2$; 50% EtOAc in hexanes) and the product was recrystallised from a mixture of dichloromethane and ethyl acetate to afford the title compound as a white solid (11.5 g). $\delta_H$ (400 MHz; CDCl$_3$) 2.86 (3H, s), 7.57 (3H, m), 7.99 (2H, m), 8.52 (1H, s). m/z (ES$^+$) 188 (M+1).

b) 5-Amino-3-methyl-6-phenyl-[1,2,4]triazine

To a solution of 3-methyl-6-phenyl-[1,2,4]triazine-4-oxide (3 g, 16 mmol) in chloroform (80 ml) was added p-toluenesulfonyl chloride (3.05 g, 16 mmol) and the mixture stirred under nitrogen at room temperature for 30 min. To this mixture was added aqueous ammonia (48 ml of 12%) and ammonia in dioxane (160 ml of a 0.5 M solution) and stirred at room temperature for 72 h. The organic layer was separated from the aqueous which was extracted with dichloromethane (2×20 ml), the combined organic layers dried over MgSO$_4$ and evaporated in vacuo. The residue was purified by flash chromatography (SiO$_2$; 20% EtOAc in hexanes) to afford the title compound (1.7 g). δ$_H$ (400 MHz; d$_6$-DMSO) 2.42 (3H, s), 6.50–7.40 (2H, vbs), 7.49–7.63 (5H, m). m/z (ES$^+$) 187 (M+1).

c) 3-Cyclopentyl-5-methyl-8-phenylimidazo[1,2-d][1,2,4]triazin-2-ol

To a solution of 5-amino-3-methyl-6-phenyl-[1,2,4]triazine (0.2 g, 1.07 mmol) in dichloromethane (20 ml) was added pyridine (0.104 ml, 1.28 mmol) followed by dropwise addition of 2-bromo-2-cyclopentylacetyl chloride (0.266 ml, 1.18 mmol; prepared from cyclopentylacetyl chloride by the method of Gleason, *Tetrahedron Lett.*, 1970, 39, 3431). The reaction mixture was stirred for 18 h after which time the dichloromethane was evaporated in vacuo. The residue was dissolved in t-butanol (20 ml) to which was added triethylamine (1 ml) and sodium iodide (0.010 g) and the resultant mixture was heated at 120° C. for 18 h. The n-butanol was evaporated in vacuo and the residue was purified by flash chromatography (SiO$_2$; 60% EtOAc in hexanes) to afford the title compound (0.178 g). δ$_H$ (400 MHz; d$_6$-DMSO) 1.40–2.20 (8H, m), 2.71 (3H, s), 3.65 (1H, m), 7.49 (3H, m), 8.05 (2H, m). m/z (ES$^+$) 295 (M+1).

d) 3-Cyclopentyl-2-(2-ethyl-2H-[1,2,4]triazol-3-ylmethoxy)-5-methyl-8-phenylimidazo[1,2-d][1,2,4]triazine To a solution of 3-cyclopentyl-5-methyl-8-phenylimidazo[1,2-d][1,2,4]triazin-2-ol (175 mg, 0.59 mmol) and 3-chloromethyl-2-ethyl-2H-[1,2,4]triazole hydrochloride (130 mg, 0.71 mmol) in anhydrous N,N-dimethylformamide under an atmosphere of nitrogen was added potassium carbonate (329 mg, 2.37 mmol). The reaction mixture was stirred at room temperature for 3 h, then evaporated in vacuo. The residue was purified by flash chromatography (SiO$_2$; 2% MeOH in CH$_2$Cl$_2$), and the product recrystallised from ethyl acetate/isohexane to afford the title compound (45 mg) as a white solid, m.p. 94–96° C.; δ$_H$ (400 MHz; CDCl$_3$) 1.44 (3H, t, J 7.2), 1.65–2.04 (8H, m), 3.01 (3H, s), 3.70 (1H, m), 4.29 (2H, q, J 7.2), 5.65 (2H, s), 7.52–7.60 (3H, m), 7.91 (1H, s), 8.10 (2H, m); m/z (ES$^+$) 404 (M$^+$+H, 100%).

EXAMPLE 26

2-(2-Ethyl-2H-[1,2,4]triazol-3-ylmethoxy)-5-methyl-8-phenyl-3-(thien-2-yl)-imidazo[1,2-d][1,2,4]triazine a) 5-Methyl-8-phenylimidazo[1,2-d][1,2,4]triazin-2-ol To a solution of 5-amino-3-methyl-6-phenyl-[1,2,4]triazine (Example 25, step b); 550 mg, 2.96 mmol) in dichloromethane was added bromoacetyl bromide (0.308 ml, 3.55 mmol), pyridine (0.357 ml, 4.44 mmol) and 4-dimethylaminopyridine (10 mg). The reaction mixture was stirred under nitrogen at room temperature for 2 h, then evaporated in vacuo. The residue was purified by flash chromatography (SiO$_2$; 40% ethyl acetate in hexanes) to yield 5-(bromoacetamido)-3-methyl-6-phenyl-[1,2,4]triazine (475 mg), m/z (ES$^+$) 307/309 (M$^+$+H). To a solution of this product (470 mg, 1.53 mmol) in 1,2-dichloroethane was added triethylamine (0.235 ml, 1.68 mmol) and sodium iodide (10 mg), and the mixture was heated at reflux for 4 h. On cooling the title compound crystallised out of solution and was collected by filtration to yield 220 mg. δ$_H$ (400 MHz; d$_6$-DMSO) 2.80 (3H, s), 7.34 (1H, s), 7.56 (3H, m), 8.54 (2H, m), 11.35 (1H, bs); m/z (ES$^+$) 227 (M$^+$+H).

b) 2-(2-Ethyl-2H-[1,2,4]triazol-3-ylmethoxy)-5-methyl-8-phenyl-imidazo[1,2-d][1,2,4]triazine By substantially following the procedures of Example 25, step d), using 5-methyl-8-phenylimidazo[1,2-d][1,2,4]triazin-2-ol in place of 3-cyclopentyl-5-methyl-8-phenylimidazo[1,2-d][1,2,4]triazin-2-ol, was prepared the title compound as a white solid. δ$_H$ (400 MHz; CDCl$_3$) 1.48 (3H, t, J 7.2), 2.87 (3H, s), 4.33 (2H, q, J 7.2), 5.62 (2H, s), 7.11 (1H, s), 7.55 (3H, m), 7.91 (1H, s), 8.61 (2H, m); m/z (ES$^+$) 336 (M$^+$+H).

c) 3-Bromo-2-(2-ethyl-2H-[1,2,4]triazol-3-ylmethoxy)-5-methyl-8-phenyl-imidazo[1,2-d][1,2,4]triazine To a solution of 2-(2-ethyl-2H-[1,2,4]triazol-3-ylmethoxy)-5-methyl-8-phenylimidazo[1,2-d][1,2,4]triazine (205 mg, 0.61 mmol) in a mixture of carbon tetrachloride (100 ml) and chloroform (50 ml) was added bromine (34.2 μl, 0.67 mmol) dropwise. The mixture was stirred for 1 h, the solvent removed in vacuo and the residue recrystallised from a mixture of diethyl ether and methanol to give the title compound (160 mg). δ$_H$ (400 MHz; d$_6$-DMSO) 1.35 (3H, t, J 7.2), 3.15 (3H, d, J 6.6), 4.31 (2H, q, J 7.2), 5.72 (2H, s), 7.58 (3H, m), 7.98 (1H, s), 8.42 (2H, m); m/z (ES$^+$) 414/416 (M$^+$+H).

d) 2-(2-Ethyl-2H-[1,2,4]triazol-3-ylmethoxy)-5-methyl-8-phenyl-3-(thien-2-yl)imidazo[1,2-d][1,2,4]triazine A mixture of 3-bromo-2-(2-ethyl-2H-[1,2,4]triazol-3-ylmethoxy)-5-methyl-8-phenylimidazo[1,2-d][1,2,4]triazine (70 mg, 0.169 mmol), 2-thiopheneboronic acid (32 mg, 0.254 mmol) and cesium carbonate (110 mg, 0.338 mmol) in anhydrous 1,4-dioxane (5 ml) was degassed using three freeze-pump-thaw cycles. Tris(dibenzylideneacetone)dipalladium(0) (15.5 mg, 0.017 mmol) and a 0.1M solution of tri-tert-butylphosphine in 1,4-dioxane (0.406 ml, 0.406 mmol) was added, and the mixture was further degassed with two more freeze-pump-thaw cycles before heating at 90° C. under nitrogen for 17 h. The mixture was filtered through glass fibre paper, washed with ethyl acetate. The filtrate was washed with saturated NaCl solution, separated, dried over MgSO$_4$ and evaporated in vacuo. The residue was purified by flash chromatography (SiO$_2$; 2% MeOH in CH$_2$Cl$_2$), and the product recrystallised from CH$_2$Cl$_2$ to afford the title compound (10.4 mg) as a white solid. δ$_H$ (400 MHz; CDCl$_3$) 1.28 (3H, t, J 7.2), 2.58 (3H, d), 4.19 (2H, q, J 7.2), 5.68 (2H, s), 7.18 (2H, m), 7.57 (4H, m), 7.89 (1H, s), 8.61 (2H, m); m/z (ES$^+$) 414/416 (M$^+$+H).

What is claimed is:

1. A compound of formula I, or a salt thereof:

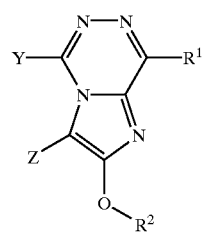

(I)

wherein

Y represents hydrogen, C$_{1-6}$ alkyl or C$_{3-7}$ cycloalkyl;

Z represents C$_{1-6}$ alkyl, C$_{3-7}$ cycloalkyl, C$_{4-7}$ cycloalkenyl, C$_{6-8}$ bicycloalkyl, aryl, C$_{3-7}$ heterocycloalkyl, heteroaryl or di(C$_{1-6}$)alkylamino, any of which groups may be optionally substituted;

R$^1$ represents C$_{3-7}$ cycloalkyl, phenyl, furyl, thienyl or pyridinyl, any of which groups may be optionally substituted; and R$^2$ represents C$_{3-7}$ cycloalkyl(C$_{1-6}$)alkyl, aryl(C$_{1-6}$)alkyl or heteroaryl(C$_{1-6}$)alkyl, any of which groups may be optionally substituted.

2. A compound as claimed in claim 1 represented by formula IIA, or a salt thereof:

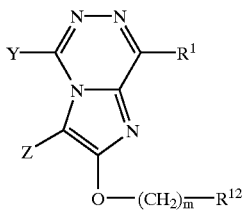
(IIA)

wherein

Y, Z and $R^1$ are as defined in claim 1;

m is 1 or 2; and $R^{12}$ represents aryl or heteroaryl, either of which groups may be optionally substituted.

3. A compound as claimed in claim 2 represented by formula IIB, or a pharmaceutically acceptable salt thereof:

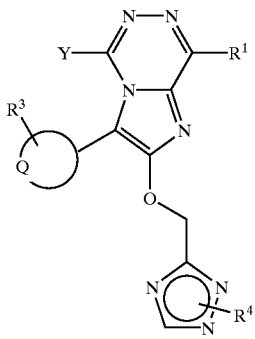
(IIB)

wherein

Y and $R^1$ are as defined in claim 1;

Q represents the residue of a cyclopropyl, cyclobutyl, cyclopentyl, cyclohexyl, phenyl or thienyl ring;

$R^3$ represents hydrogen, methyl, fluoro or chloro; and $R^4$ represents hydrogen, methyl or ethyl.

4. A compound as claimed in claim 2 represented by formula IIC, or a pharmaceutically acceptable salt thereof:

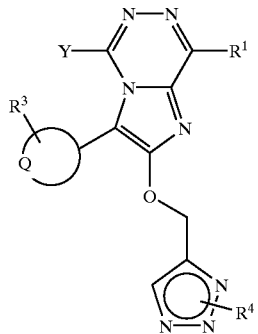
(IIC)

wherein

Y and $R^1$ are as defined in claim 1; and

Q, $R^3$ and $R^4$ are as defined in claim 3.

5. A compound selected from:

3,8-diphenyl-2-(2-methyl-2H-[1,2,4]triazol-3-ylmethoxy)imidazo[1,2-d][1,2,4]triazine;

8-(2-fluorophenyl)-2-(2-methyl-2H-[1,2,4]triazol-3-ylmethoxy)-3-phenyl-imidazo[1,2-d][1,2,4]triazine;

8-(2-fluorophenyl)-2-(1-methyl-1H-[1,2,4]triazol-3-ylmethoxy)-3-phenyl-imidazo[1,2-d][1,2,4]triazine;

8-(2,5-difluorophenyl)-2-(2-methyl-2H-[1,2,4]triazol-3-ylmethoxy)-3-phenylimidazo[1,2-d][1,2,4]triazine;

8-(4-fluorophenyl)-2-(2-methyl-2H-[1,2,4]triazol-3-ylmethoxy)-3-phenyl-imidazo[1,2-d][1,2,4]triazine;

8-(2,6-difluorophenyl)-2-(2-methyl-2H-[1,2,4]triazol-3-ylmethoxy)-3-phenylimidazo[1,2-d][1,2,4]triazine;

3-cyclobutyl-8-(2-fluorophenyl)-2-(2-methyl-2H-[1,2,4]triazol-3-ylmethoxy)-imidazo[1,2-d][1,2,4]triazine;

3-(3-chlorophenyl)-2-(2-methyl-2H-[1,2,4]triazol-3-ylmethoxy)-8-phenyl-imidazo[1,2-d][1,2,4]triazine;

3-cyclobutyl-5-methyl-2-(2-methyl-2H-[1,2,4]triazol-3-ylmethoxy)-8-phenylimidazo[1,2-d][1,2,4]triazine;

3-cyclopentyl-5-methyl-2-(2-methyl-2H-[1,2,4]triazol-3-ylmethoxy)-8-phenylimidazo[1,2-d][1,2,4]triazine;

8-(2-fluorophenyl)-5-methyl-2-(2-methyl-2H-[1,2,4]triazol-3-ylmethoxy)-3-phenylimidazo[1,2-d][1,2,4]triazine;

or a salt thereof.

6. A compound selected from:

3-cyclopentyl-5-ethyl-2-(2-ethyl-2H-[1,2,4]triazol-3-ylmethoxy)-8-phenylimidazo[1,2-d][1,2,4]triazine;

3-cyclopentyl-5-ethyl-2-(2-methyl-2H-[1,2,4]triazol-3-ylmethoxy)-8-phenylimidazo[1,2-d][1,2,4]triazine;

3-cyclopentyl-5-cyclopropyl-2-(2-methyl-2H-[1,2,4]triazol-3-ylmethoxy)-8-phenylimidazo[1,2-d][1,2,4]triazine;

3-cyclopentyl-8-(2,6-difluorophenyl)-5-methyl-2-(2-methyl-2H-[1,2,4]triazol-3-ylmethoxy)imidazo[1,2-d][1,2,4]triazine;

3-cyclohexyl-8-(2-fluorophenyl)-5-methyl-2-(2-methyl-2H-[1,2,4]triazol-3-ylmethoxy)imidazo[1,2-d][1,2,4]triazine;

3,8-bis(2-fluorophenyl)-5-methyl-72-(2-methyl-2H-[1,2,4]triazol-3-ylmethoxy)imidazo[1,2-d][1,2,4]triazine;

3-cyclopentyl-8-(2,6-difluorophenyl)-2-(2-ethyl-2H-[1,2,4]triazol-3-ylmethoxy)-5-methylimidazo[1,2-d][1,2,4]triazine;

3-cyclopentyl-8-(2-fluorophenyl)-5-methyl-2-(3-methyl-3H-[1,2,3]triazol-4-ylmethoxy)imidazo[1,2-d][1,2,4]triazine;

3-cyclopentyl-8-(2-fluorophenyl)-5-methyl-2-(1-methyl-1H-[1,2,4]triazol-3-ylmethoxy)imidazo[1,2-d][1,2,4]triazine;

3-cyclopentyl-8-(2-fluorophenyl)-5-methyl-2-(1-methyl-1H-[1,2,3]triazol-4-ylmethoxy)imidazo[1,2-d][1,2,4]triazine;

3-cyclopentyl-2-(2-ethyl-2H-[1,2,4]triazol-3-ylmethoxy)-8-(2-fluorophenyl)-5-methylimidazo[1,2-d][1,2,4]triazine;

3-cyclopentyl-8-(2-fluorophenyl)-5-methyl-2-(2-methyl-2H-[1,2,4]triazol-3-ylmethoxy)imidazo[1,2-d][1,2,4]triazine;

3-cyclohexyl-2-(2-ethyl-2H-[1,2,4]triazol-3-ylmethoxy)-8-(2-fluorophenyl)-5-methylimidazo[1,2-d][1,2,4]triazine;

3-cyclopentyl-2-(2-ethyl-2H-[1,2,4]triazol-3-ylmethoxy)-5-methyl-8-phenyl-imidazo[1,2-d][1,2,4]triazine;

2-(2-ethyl-2H-[1,2,4]triazol-3-ylmethoxy)-5-methyl-8-phenyl-3-(thien-2-yl)-imidazo[1,2-d][1,2,4]triazine;

or a salt thereof.

7. A pharmaceutical composition comprising a compound of formula I as defined in claim 1 or a pharmaceutically acceptable salt thereof in association with a pharmaceutically acceptable carrier.

8. A process for the preparation of a compound as claimed in claim 1, which comprises:

(A) reacting a compound of formula III with a compound of formula IV:

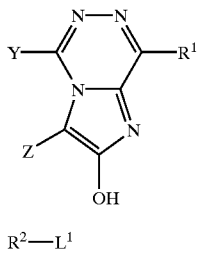

(III)

$R^2$—$L^1$ (IV)

wherein Y, Z, $R^1$ and $R^2$ are as defined in claim 1, and $L^1$ represents a suitable leaving group; or (B) reacting a compound of formula III as defined above with a compound of formula V:

$R^2$—OH (V)

wherein $R^2$ is as defined in claim 1; in the presence of triphenylphosphine and diethyl azodicarboxylate; or (C) reacting a compound of formula VIII with a compound of formula IX:

Z—B(OH)$_2$ (VIII)

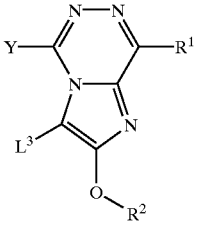

(IX)

wherein Y, Z, $R^1$ and $R^2$ are as defined in claim 1, and $L^3$ represents a suitable leaving group; in the presence of a transition metal catalyst; and (D) subsequently, if desired, converting a compound of formula I initially obtained into a further compound of formula I by standard methods.

9. A method for the treatment of anxiety, which comprises administering to a patient in need of such treatment an effective amount of a compound of formula I as defined in claim 1 or a pharmaceutically acceptable salt thereof.

* * * * *